US00PP08075P

United States Patent [19]

McGredy, IV

[11] Patent Number: Plant 8,075

[45] Date of Patent: Dec. 29, 1992

[54] HYBRID TEA ROSE PLANT NAMED MACGREMLI

[75] Inventor: Sam McGredy, IV, Auckland, New Zealand

[73] Assignee: DeVor Nurseries, Inc., Watsonville, Calif.

[21] Appl. No.: 704,468

[22] Filed: May 23, 1991

[51] Int. Cl.[5] ..... A01H 5/00

[52] U.S. Cl. ..... Plt./12

[58] Field of Search ..... Plt. 11, 12, 13

[56] References Cited

U.S. PATENT DOCUMENTS

P.P. 3,847 3/1976 Swim et al. ..... Plt. 11

*Primary Examiner*—Howard J. Locker

*Attorney, Agent, or Firm*—Christie, Parker & Hale

[57] ABSTRACT

A new variety of hybrid tea rose having yellow-orange red bicolored flowers.

1 Drawing Sheet

SUMMARY OF THE INVENTION

The present invention relates to a new and distinct variety of rose plant of the hybrid tea rose class, which was originated by my crossing as seed parent the variety known as "Macsatur" and as pollen parent the variety known as "Macputar". The varietal denomination of this new rose is "Macgremli".

Among the novel characteristics possessed by this new variety which distinguishes it from its parents and all other varieties of which I am aware are its attractive bicolor flowers having orange-red coloring on the petals top surface and yellow coloring on the petal's reverse (under surface). The flowers are borne singly in a manner typical of hybrid tea varieties and on a plant suitable for growing outdoors in gardens.

Asexual reproduction by propagation by budding of the new variety as performed in Santa Cruz County, Calif. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character.

DETAILED DESCRIPTION OF THE NEW VARIETY

The following is a detailed description of my new variety, with color terminology in accordance with the Royal Horticultural Society Colour Chart (RHSCC). The terminology used in the color description herein refers to plate numbers in the aforementioned color chart.

Parentage: Seedling.

*Seed.*—"Macsatur."

*Pollen parent.*—"Macputar."

Class: Hybrid tea.

The following further horticultural observations were made of specimens grown outdoor in Santa Cruz County, Calif. in the months of May through November.

FLOWER

Blooming habit: Recurrent.

A. Bud:

(1) *Size.*—Medium; about 1.8 inches long×about 1.2 inches wide.

(2) *Form.*—Ovoid.

(3) *Color.*—As sepals first divide, near 40B; after petals begin to unfurl, near 40B.

(4) *Sepals.*—Majority are pointed, few are ovate — acuminate; longer than bud — about 1.7 to 1.9 inches.

(5) *Peduncle.*—Length — about 2.9 inches. Aspect — straight, very fine prickles. Strength — erect. Color — near 199A at very top, balance near 146D.

B. Bloom:

(1) *Size.*—Average size when fully expanded — about 5.3 inches.

(2) *Borne.*—Singly, one to a stem.

(3) *Form.*—Imbricated, at first petals loosely roll outward then become ruffled at maturity.

(4) *Petalage.*—Number of petals under normal conditions — about 38 to 43.

(5) *Color.*—After sepals fall and petals unfurl, predominant flower color viewing petals' top surface is near 40A. As flowers open petals' reverse surface, near 7A, becomes visible. Bicoloration is substantially stable and constant. Petal color near point of petal attached is near 2D. General tonality from a distance is attractive yellow-orange red bicoloration. As blooms age, outer petal edge at top surface tends toward near 43A with balance near 43C; after three or more days, coloration at outer petal edge and balance of petal (top surface) becomes near 48A and 51B, respectively. Petal undersurface tends toward near 4A upon aging.

C. Petals:

(1) *Texture.*—Thick, firm.

(2) *Appearance.*—Inside velvety and outside matte.

(3) *Form.*—Slightly lobed, heart shaped.

(4) *Arrangement.*—Regularly arranged, imbricated.

(5) *Petaloids in center.*—Medium, cupped over reproductive organs.

(6) *Persistence.*—Drop off cleanly.

(7) *Fragrance.*—Slight, sweet scent.

(8) *Lasting quality.*—Very long lasting on plant.

REPRODUCTIVE ORGANS

A. Stamens, filaments and anthers:
*Arrangement.*—Regularly arranged around styles — introrse anthers.
*Color.*—Near 21A.

B. Pollen:
*Color.*—Near 22A.

C. Styles: Uneven lengths, 0.1 to 0.4 inches.

D. Stigmas: Near 162B.

E. Hips: Sparse, urn-shaped, bright orange, scarlet.

PLANT

A. Form: Upright.

B. Growth: Vigorous.
*Height attained.*—About 5 feet.

C. Foliage: Mostly compound 5 leaflets.
(1) *Size.*—Large.
(2) *Quantity.*—Abundant.
(3) *Color.*—New foliage: Upper side — near 146B. Under side — near 148B. Old foliage: Upper side — near 147A. Under side — near 148A.
(4) *Shape.*—Mucronata.
(5) *Texture.*—Upper side is shiny, smooth; under side is matte.
(6) *Edge.*—Serrate.

(7) *Serration.*—Dentate.
(8) *Leaf stem.*—Color — near 176B with near 146C underside.
(9) *Stipules.*—Medium, long auricles.
(10) *Resistance to disease.*—Blackspot — moderate. Mildew — susceptible. Rust — moderate.

D. Wood:
(1) *New wood.*—Color — near 146B. Bark — smooth.
(2) *Old wood.*—Color — near 146C. Bark — smooth.

E. Thorns:
*Quantity (main stalk).*—Ordinary, about 36 may be counted.
*On laterals from stalk.*—few.
*Form.*—Flat base — dilated.
*Length.*—Most are large, some small.
*Color.*—Near 176B.
*Position.*—Irregular.
*Prickles.*—Few on main stalks and laterals.

F. Winter hardiness: Winter hardy in Santa Cruz County, Calif.

I claim:

1. A new and distinct variety of rose plant of the hybrid tea rose class, substantially as shown and described.

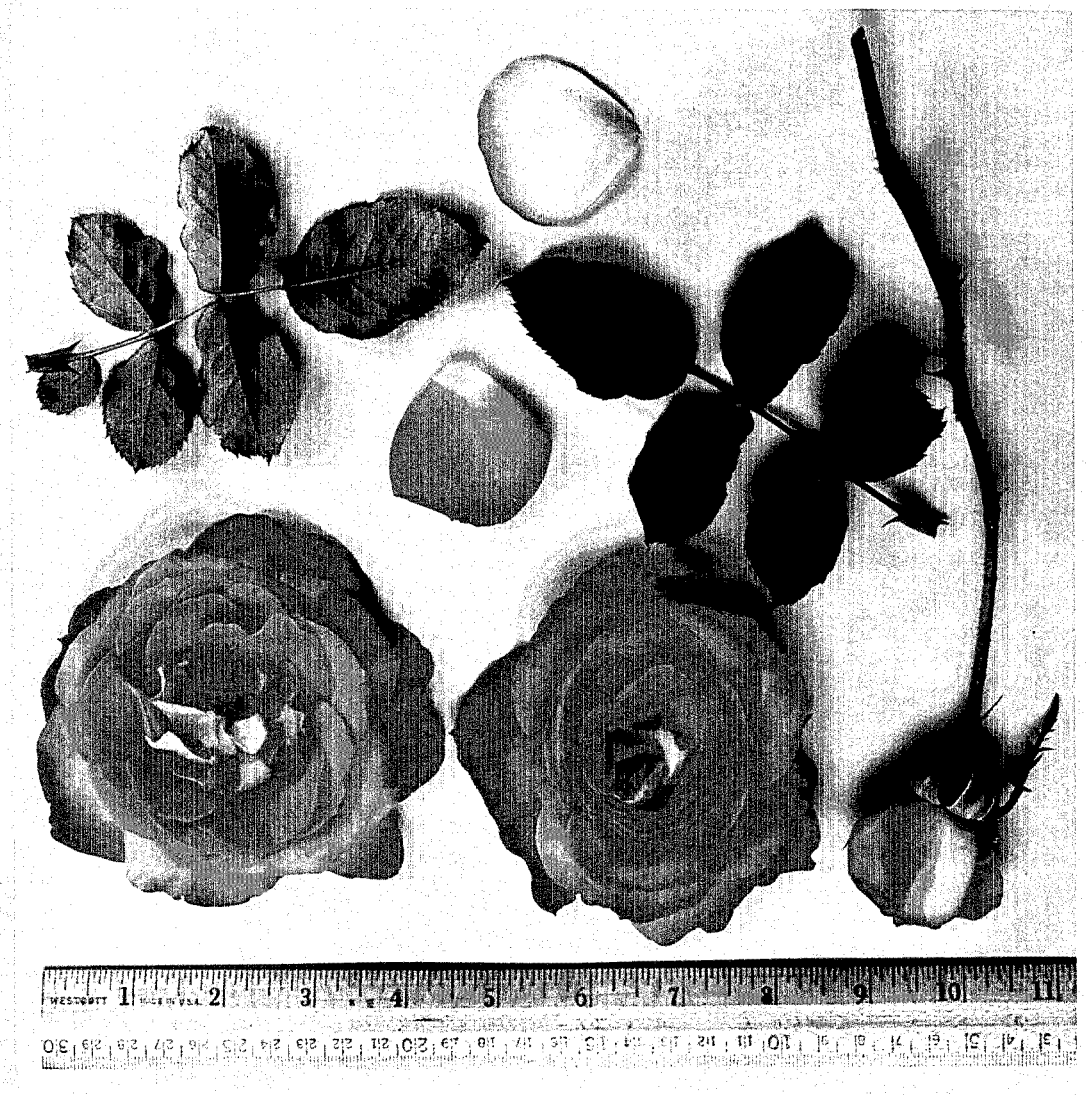

* * * * *